United States Patent
Weijand et al.

(10) Patent No.: US 6,484,054 B2
(45) Date of Patent: Nov. 19, 2002

(54) DEEP TRENCH SEMICONDUCTOR CAPACITORS HAVING REVERSE BIAS DIODES FOR IMPLANTABLE MEDICAL DEVICES

(75) Inventors: Koen J. Weijand, Hellevoetsluis (NL); Richard Houben, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/879,282

(22) Filed: Jun. 12, 2001

(65) Prior Publication Data

US 2002/0008267 A1 Jan. 24, 2002

Related U.S. Application Data

(60) Provisional application No. 60/210,732, filed on Jun. 12, 2000.

(51) Int. Cl.[7] .................................................. A61N 1/00
(52) U.S. Cl. .......................................................... 607/2
(58) Field of Search ................................ 600/300–595; 607/1–156

(56) References Cited

U.S. PATENT DOCUMENTS

| | | |
|---|---|---|
| 5,394,000 A | 2/1995 | Ellul et al. |
| 5,941,906 A | 8/1999 | Barreras, Sr. et al. |
| 5,948,004 A | 9/1999 | Weijand et al. |
| 5,964,787 A | 10/1999 | Kerver et al. |
| 6,121,106 A | 9/2000 | Ellis et al. |

OTHER PUBLICATIONS

High–Value MOS Capacitor in Ultra–Deep Trenches in Silicon to Roozeboom et al., Philips Research, The Netherlands.

*Primary Examiner*—Scott M. Getzow
(74) *Attorney, Agent, or Firm*—Thomas F. Woods; Eric R. Waldkoetter; Tom G. Berry

(57) ABSTRACT

Floating and non-floating on-chip capacitors are formed by vertical walls and/or large aspect ratio deep trenches disposed in semiconductor material. By optimizing the through spacing and substrate voltage, a very small parasitic to intended capacitance ratio may be obtained. Capacitors so formed may be used as on-chip charge storage and other types of on-chip capacitors, and eliminate or reduce the number of off-chip capacitors that would otherwise be required. The deep trench capacitors find particularly efficacious application in implantable medical devices where volume, cost and electrical energy consumption must be minimized, and preferably have capacitances which range between about 10 nF and about 1000 uF.

36 Claims, 14 Drawing Sheets

DEEP TRENCH SEMICONDUCTOR CAPACITORS HAVING REVERSE BIAS DIODES FOR IMPLANTABLE MEDICAL DEVICES

RELATED APPLICATIONS

This patent application claims priority and other benefits from U.S. Provisional Patent Application Ser. No. 60/210, 732 entitled "Applications of Integrated MOS Capacitor Arrays Including On-Chip Energy management, Circuit Decoupling and Switch Capacitor Circuits" to Weijand et al. filed Jun. 12, 2000, and incorporates the entirety of same by reference herein.

FIELD OF THE INVENTION

This invention is generally directed to the field of capacitors for integrated circuits and semiconductors, and is more particularly directed to the field of vertically integrated capacitors in such circuits and semiconductors.

BACKGROUND OF THE INVENTION

It is a well known in the filed of implantable medical devices that device volume and electrical energy consumption must be minimized if the implantable device is to prove efficacious and beneficial. Moreover, implantable medical device reliability must be high, as patient's lives often literally depend on the continuing operation of the device. Additionally, manufacturing and material costs in such devices must be held to a minimum if they are to be affordable and therefore available to a wide range of patients having different demographic characteristics.

Semiconductors are employed extensively in many implantable medical devices. Because most implantable medical devices either sense or deliver electrical charges or electromagnetic fields to various types of human tissue, capacitors find widespread application in these devices. Owing to total charge capacity and other requirements, however, such capacitors are often difficult or impossible to physically integrate on a cost-effective basis into the semiconductor materials employed to form the integrated circuits or chips widely employed in implantable medical devices. Instead, off-chip capacitors are typically employed that are wire-bonded to integrated circuits. Among other things, such off-chip capacitor configurations result in increased parasitic capacitances, high switching losses, and significant increases in the volumes and areas of integrated circuits owing to the presence of wire bond pads and physically large capacitors. What is needed is a means of eliminating off-chip capacitors in implantable medical and other devices, thereby reducing the cost, physical size and volume of such devices.

Patents and printed publications describing various aspects of the foregoing problems and the state of the art are listed below.

1. High-Value MOS Capacitor in Ultra-Deep Trenches in Silicon to Rosseboom et al., Philips Research.
2. U.S. Pat. No. 5,394,000 entitled "Trench Capacitor Structure" to Ellul et al.
3. U.S. Pat. No. 6,121,106 entitled "Method for Forming an Integrated Trench Capacitor" to Ellis.
4. U.S. Pat. No. 5,964,787 entitled "Stimulus with Controllable Switched Capacitor Output Stage" to Kerver et al.
5. U.S. Pat. No. 5,948,004 entitled "Implantable Stimulator Having an Efficient Output Generator" to Weijand et al.
6. U.S. Pat. No. 5,941,906 entitled "Implantable Modular Tissue Stimulator" to Barreras et al.

Broadly, it is the object of the present invention to provide an improved integrated circuit for implantable medical and other devices which eliminates or substantially reduces the number of off-chip capacitors. It is a yet further object of the present invention to provide an integrated circuit for an implantable medical or other device, which is smaller and less expensive than prior art integrated circuits.

All patents and printed publications listed hereinabove are hereby incorporated by reference herein, each in its respective entirety. As those of ordinary skill in the art will appreciate readily upon reviewing the drawings set forth herein and upon reading the Summary of the Invention, Detailed Description of the Preferred Embodiments and Claims set forth below, at least some of the devices and methods disclosed in the patents and publications listed hereinabove may be modified advantageously in accordance with the teachings of the present invention.

SUMMARY OF THE INVENTION

Various embodiments of the present invention have certain objects. That is, various embodiments of the present invention provide solutions to problems existing in the prior art, including, but not limited to, the problems listed above.

Various embodiments of the present invention have certain advantages, including, without limitation, one or more of: (a) reducing the size of devices which include integrated circuits; (b) reducing the number of wire bond pads; (c) increasing the manufacturing yield of devices which include integrated circuits as a result of reducing the number of wire bond pad connections that must be made; (d) increasing the density of integrated circuits; (e) reducing the cost of integrated circuits; (f) reducing the size of implantable medical devices; and (f) increasing the reliability of implantable medical devices.

Various embodiments of the present invention have certain features, including one or more of the following: (a) deep trench floating capacitors formed in semiconductor materials; (b) high aspect ratio deep trench floating capacitors formed in semiconductor materials; (c) deep trench non-floating capacitors formed in semiconductor materials; (b) high aspect ratio deep trench non-floating capacitors formed in semiconductor materials; (c) integrated circuits connected to a minimum number of off-chip capacitors via wire bond or other means; (d) on-chip input capacitors for implantable medical stimulators and defibrillators; (e) on-chip output capacitors for implantable medical stimulators and defibrillators; (f) on-chip power supply bypassing and decoupling capacitors; (g) on-chip charge transfer capacitors; (h) on-chip charge storage capacitors; and (i) on-chip DC blocking output capacitors.

Floating and non-floating on-chip capacitors are formed by vertical walls and/or large aspect ratio trenches disposed in semiconductor material. By optimizing the through spacing and substrate voltage, a very small parasitic to intended capacitance ratio may be obtained. Capacitors so formed may be used as on-chip charge storage and other types of on-chip capacitors, and eliminate or reduce the number of off-chip capacitors that would otherwise be required. The capacitors find particularly efficacious application in implantable medical devices where volume, cost and electrical energy consumption must be minimized.

BRIEF DESCRIPTION OF THE DRAWINGS

The present invention will become better understood by reference to the following Detailed Description of the Preferred Embodiments of the present invention when considered in connection with the accompanying Figures, in which like numbers designate like parts throughout, and where.

DETAILED DESCRIPTION OF THE PREFERRED EMBODIMENTS

Figure 1:
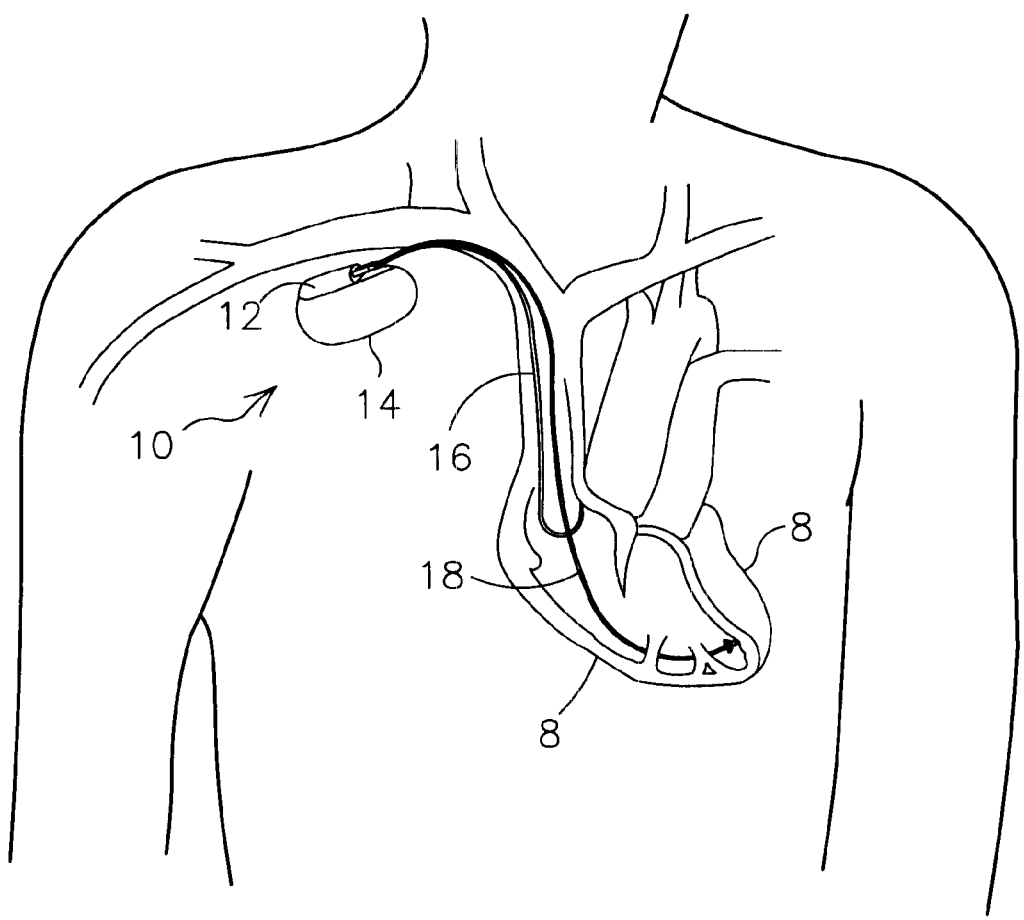
FIG. 1 shows a simplified schematic view of one embodiment of an IMD that may be employed in conjunction with the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
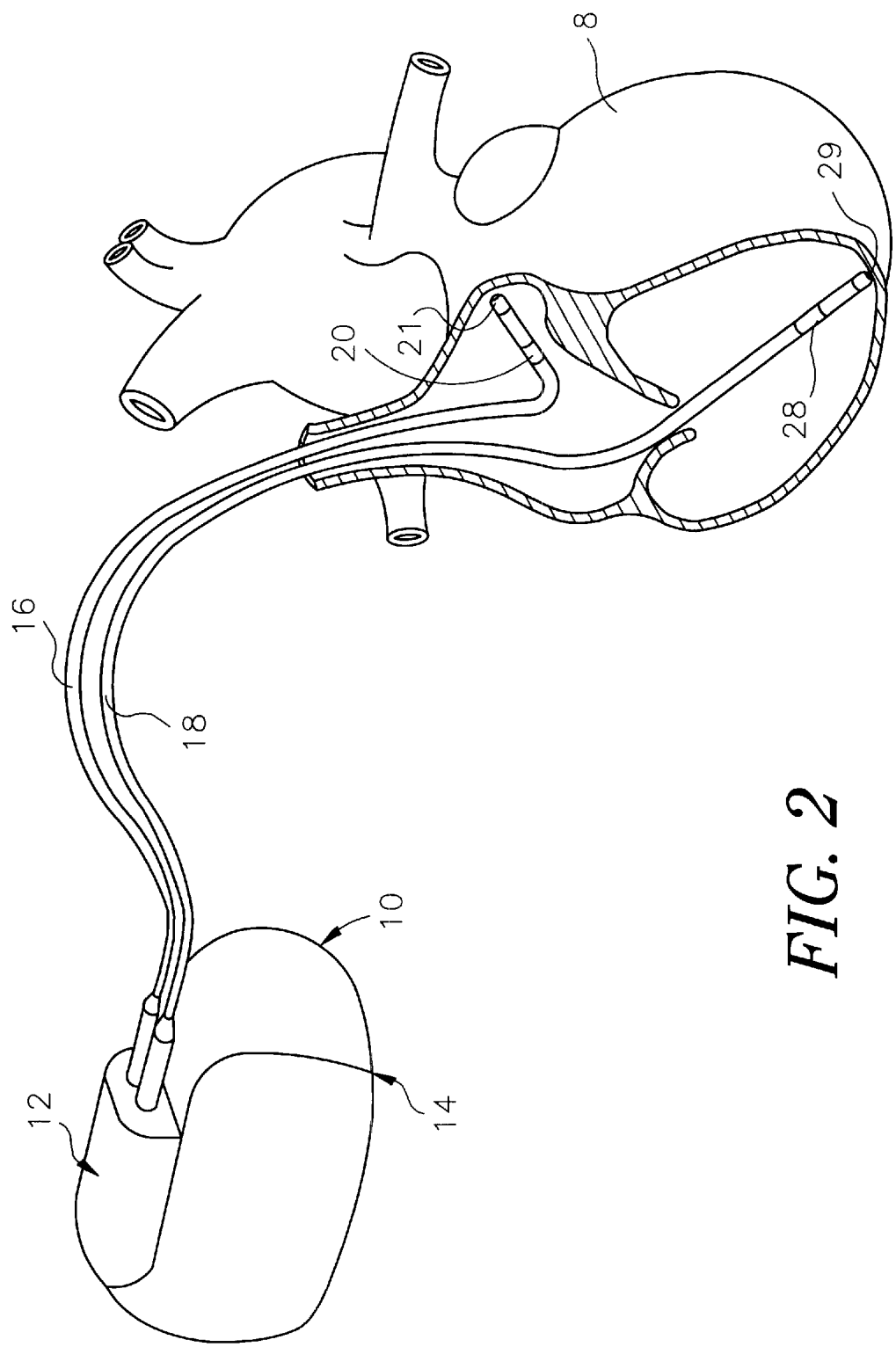
FIG. 2 shows a simplified illustration of an IMD with medical electrical leads positioned within passageways of a heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
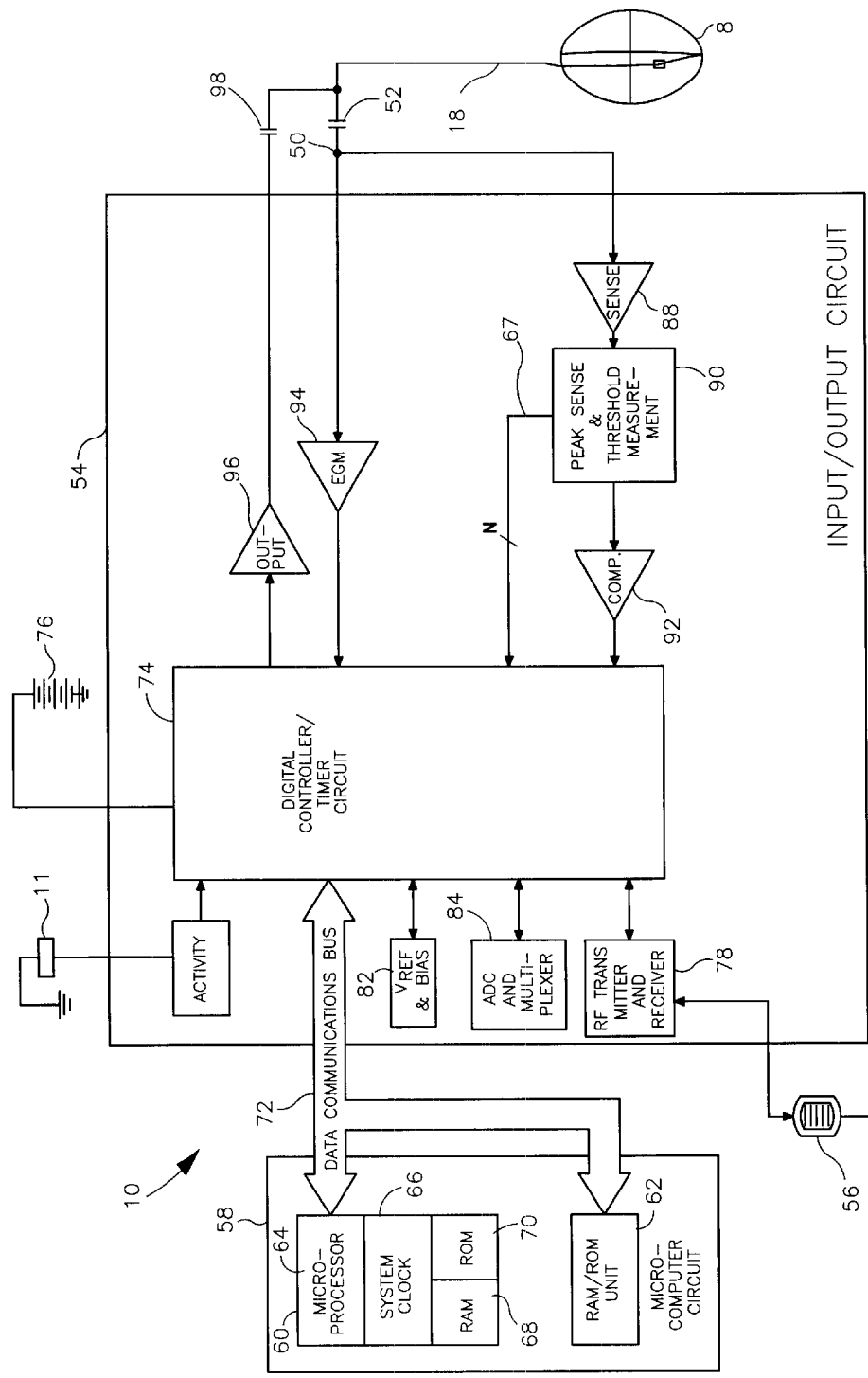
FIG. 3 shows a block diagram illustrating some constituent components of an IMD.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wybomy et al., hereby incorporated by reference herein in its entirety. The programming methodology disclosed in Wybomy et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wybomy et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. patents referenced therein.

IMD 10 may also be a pacemaker-cardioverter- defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
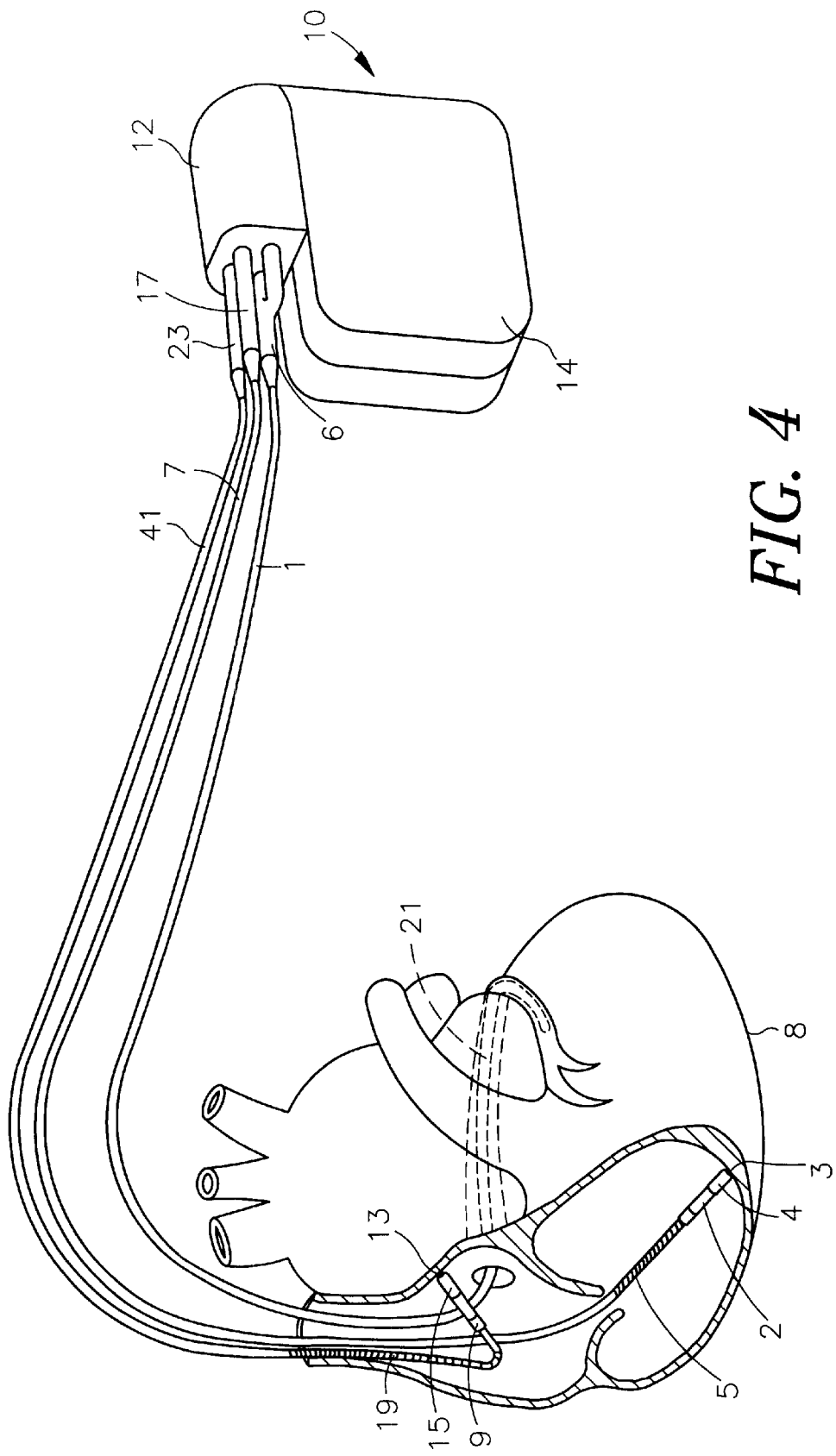
FIG. 4 shows a simplified schematic view of an IMD with medical electrical leads positioned within passageways of a heart.
Figure 5:
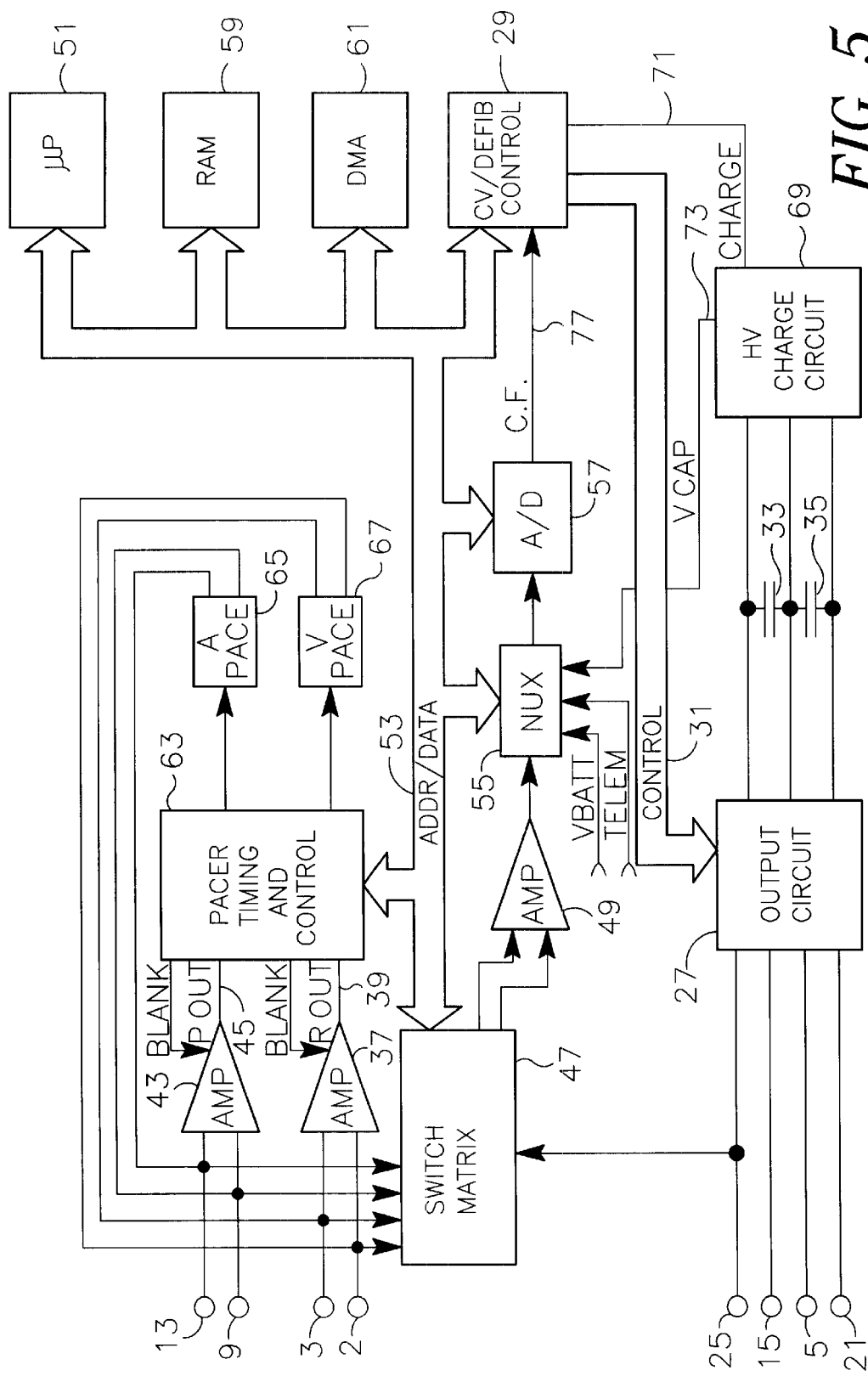
FIG. 5 shows a partial block diagram illustrating one embodiment of an IMD that may be employed in conjunction with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Turning now to the on-chip capacitor aspect of the present invention, we note at the outset that capacitors 76, 98 and 52 of FIG. 3, typically deployed as discrete capacitors wire bonded to an IC, as well as other capacitors, are well suited for adaptation as on-chip deep trench capacitors of the present invention. We note further that programmed voltage storage capacitors C1, C2, C3 and C4 in Output Mux 48 shown in FIG. 2 of U.S. Pat. No. 5,941,906 are also well suited for adaptation as on-chip deep trench capacitors of the present invention.

Figure 6:
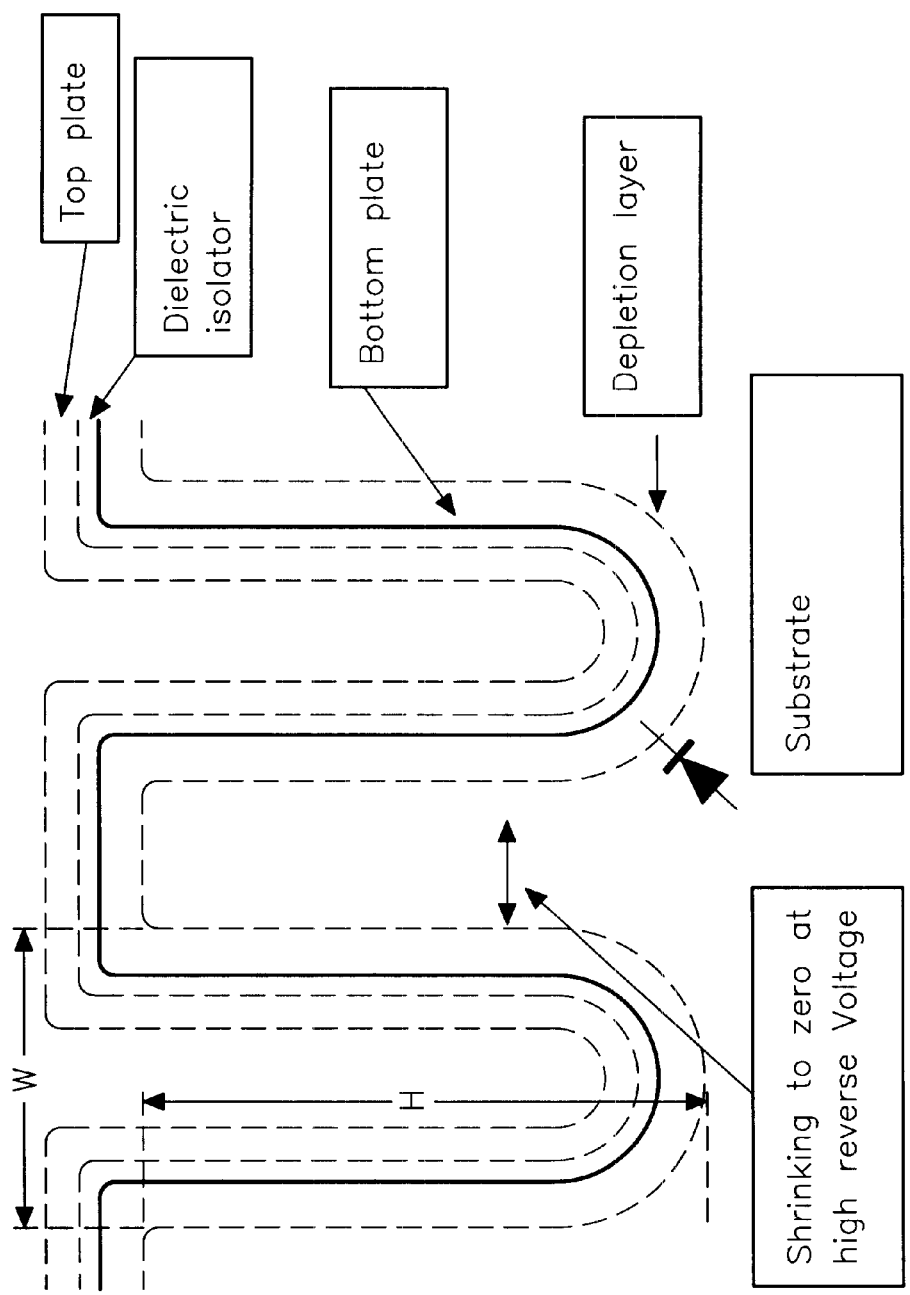
FIG. 6 shows a cross-sectional view of one representative embodiment of a deep trench capacitor of the present invention.

Referring now to FIG. 6, there is shown a cross-sectional view (not to scale) of one representative embodiment of a deep trench capacitor of the present invention. Using semiconductor processes well known in the art, the trench walls are lined with a highly conductive diffusion to form the bottom plate. A silotar or dielectric isolation layer is formed on top of the bottom layer. An appropriate metal is deposited on top of the isolation layer to create the top plate. Between the bottom plate and the substrate there is disposed a parasitic diode which is preferably normally polarized or biased in a reversed or non-conductive configuration. A depletion layer is formed between the substrate and the bottom plate, the thickness of the depletion layer depending on the reverse voltage applied to the parasitic diode. Increasing the applied reverse voltage increases the thickness of the depletion layer, and the application of the reverse voltage may proceed to such a point that the boundaries of adjoining depletion layer trenches engage, touch and merge into one another. As a result, the area of the vertical wall is depleted to such an extent that the total surface area of the parasitic capacitor is reduced. Through proper selection of trench position the wall to wall distance of the resulting trench capacitor may be determined.

One standard application of deep trench capacitors is single ended DRAMs. In one embodiment of the present invention, an extra bottom electrode or parasitic diode is added to a known deep trench capacitor to form a deep trench capacitor of the present invention to thereby form a floating deep trench capacitor which is electrically isolated from any other similarly formed deep trench capacitors formed in the same substrate. In another embodiment of the present invention, selected similarly configured and formed deep trench capacitors having bottom electrodes or parasitic diodes are not floating, but are instead are connected electrically to one another via series or parallel connections formed in the substrate which is common to the electrically connected deep trench capacitors. All deep trench capacitors of the present invention are distinguished or characterized by the bottom electrode or diode formed at or near the bottom of the deep trench, where the electrode or diode is reverse biased.

Note that the aspect ratios, or the ratios of the height H and width W of the deep trench semiconductor capacitors of the present invention, may range between about 5 and about 1000, more preferably ranges between about 10 and about 500 and most preferably ranges between about 20 and about 250, and most preferably range between about 30 and about 100. The trenches of the present invention typically range between about 100 micrometers and about 500 micrometers high (H), and typically range between about 2 micrometers and about 5 micrometers wide (W). An n+ type diffusion is preferably applied to the top of the substrate to form a conductive layer, thereby forming a diode between the n+ region and the underlying p substrate. Preferred capacitances of the deep trench capacitors of the present invention range between about 10 nF and about 1000 uF FIGS. 7a through 7f show cross-sectional views corresponding to various steps of one representative method of forming an on-chip capacitor of the present invention.

Figure 7A:
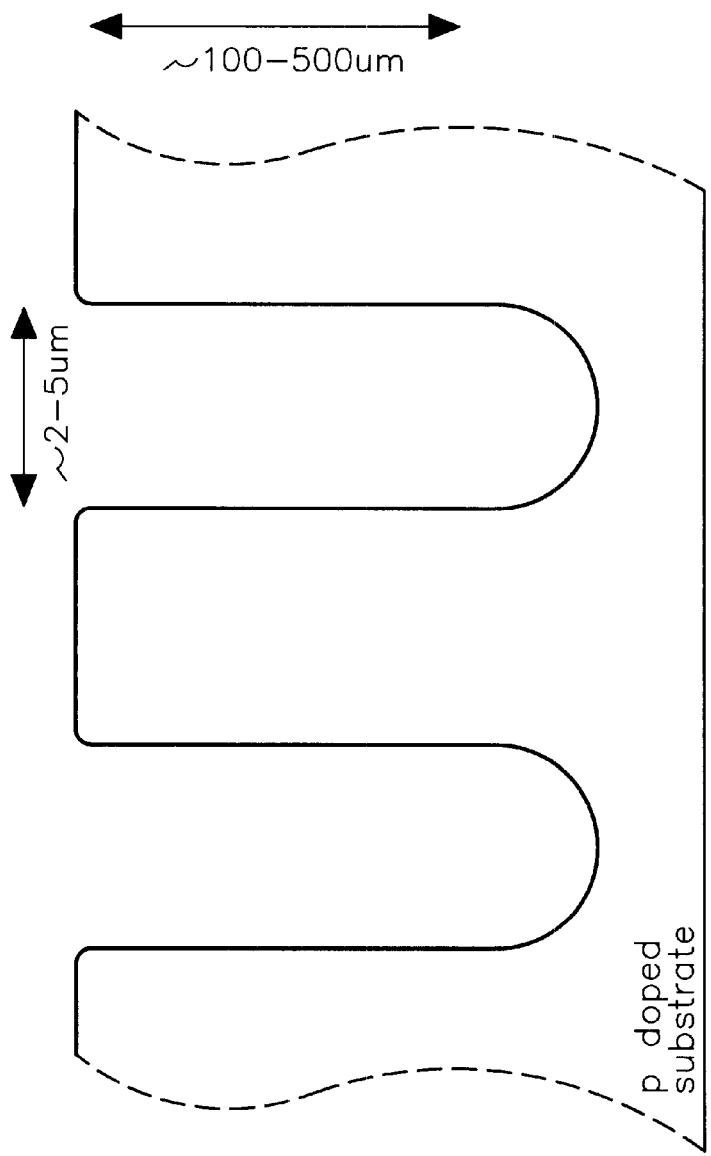
FIGS. 7a through 7f show cross-sectional views corresponding to various steps of one representative method of forming an on-chip capacitor of the present invention.

In FIG. 7a there is shown a standard p-doped silicon for CMOS circuits employed as the substrate material in which the deep trench capacitors of the present invention are to be formed. Not that while in the drawings p-doped substrate material is illustrated, n-type substrate material may also be employed. The method of the present invention finds particularly efficacious application in conjunction with the macroporous silicon and other materials and processes described by Philips Research Labs of Eindhoven, the Netherlands in their publication and presentation entitled "High-Value MOS Capacitor in Ultra-Deep Trenches in Silicon" to Rosseboom et al., the entirety of which is hereby incorporated by reference herein. As mentioned above, the trenches of the present invention typically range between about 100 micrometers and about 500 micrometers high (H), and typically range between about 2 micrometers and about 5 micrometers wide (W).

Figure 7B:
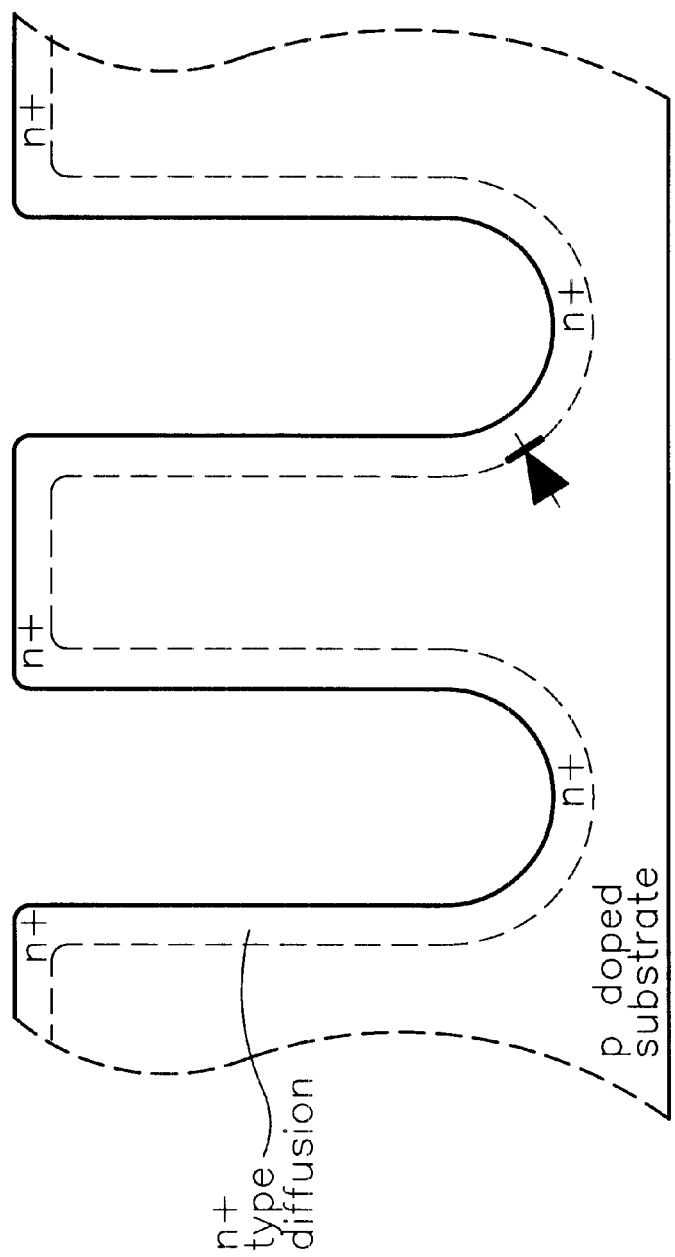
Figure 7C:
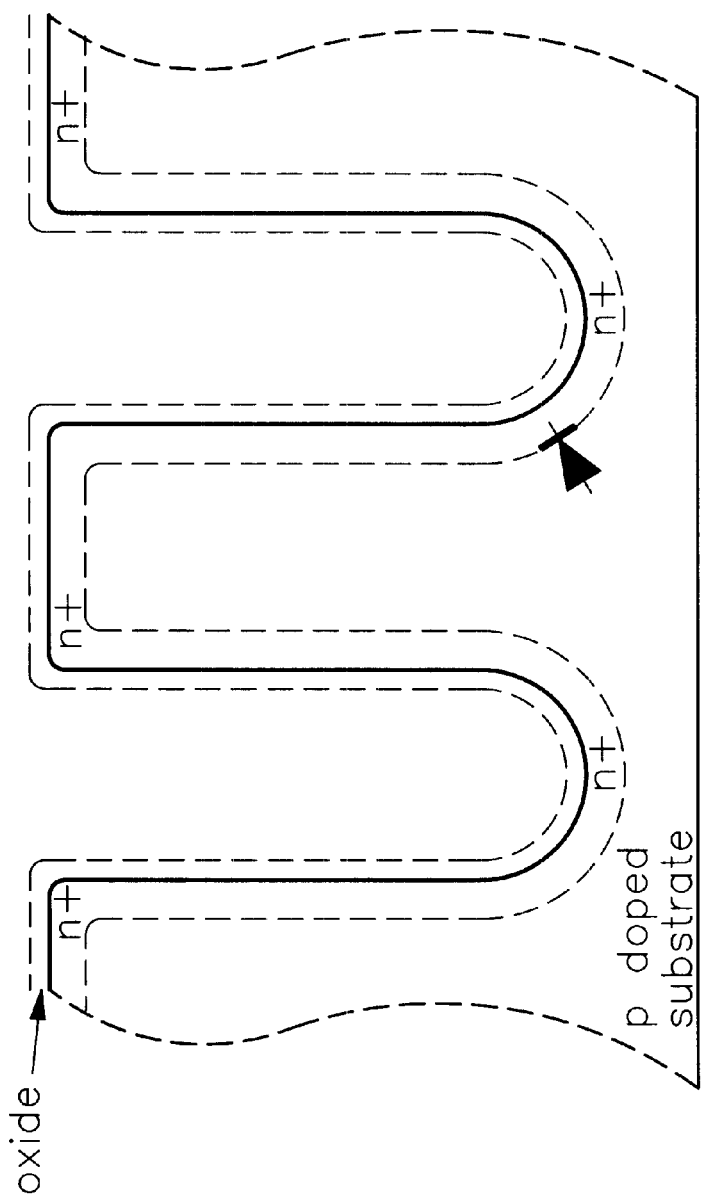
Figure 7D:
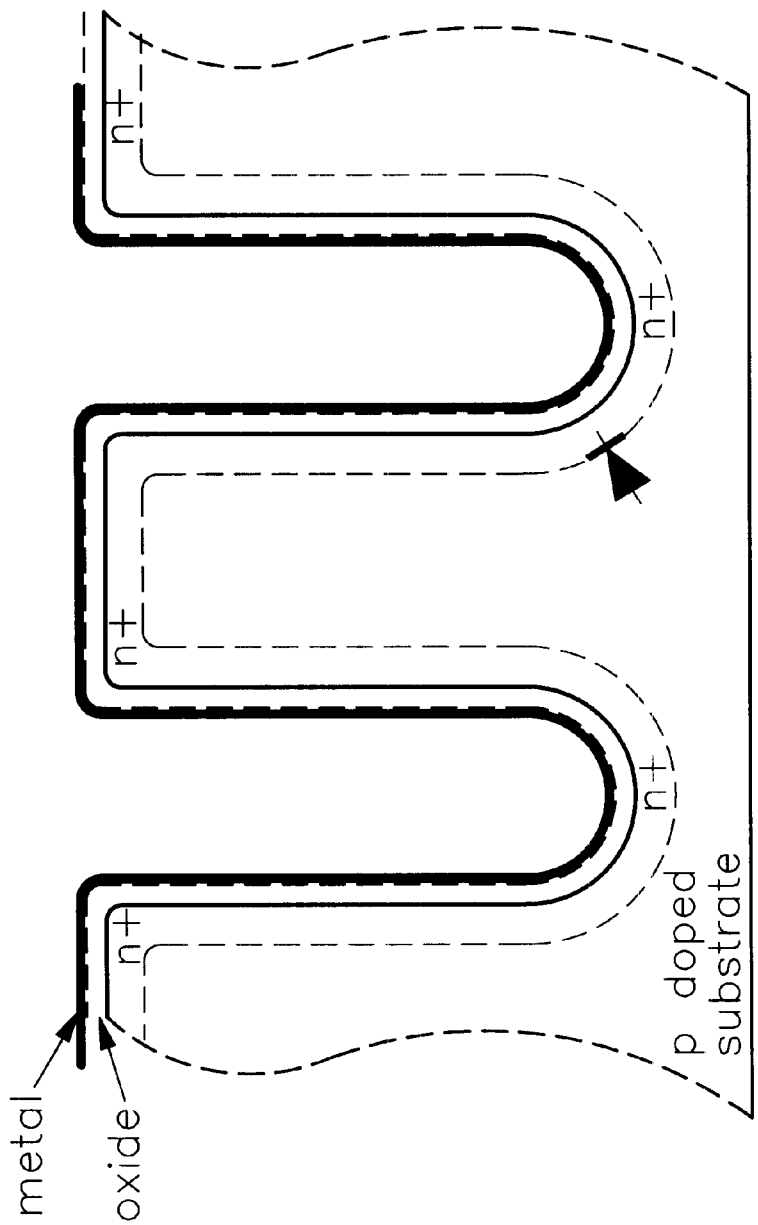

FIG. 7b shows the cross-sectional view of FIG. 7a, with an n+ type diffusion is applied to the top of the p-doped substrate to form a conductive layer, thereby forming a diode between the n+ region and the underlying p substrate. FIG. 7c shows an additional oxide layer grown on the surface of the p-doped substrate with n+ type diffusion to form the dielectric layer of the intended deep trench capacitor. FIG. 7d shows the cross-sectional view of FIG. 7c, with a suitable metal layer deposited atop the additional oxide layer to thereby form the top plate of the deep trench capacitor. In accordance with semiconductor manufacturing techniques well known in the art, contact holes may be etched through the metal and oxide layers to permit electrical access and connection to the lower n+ type diffusion layer.

Figure 7E:
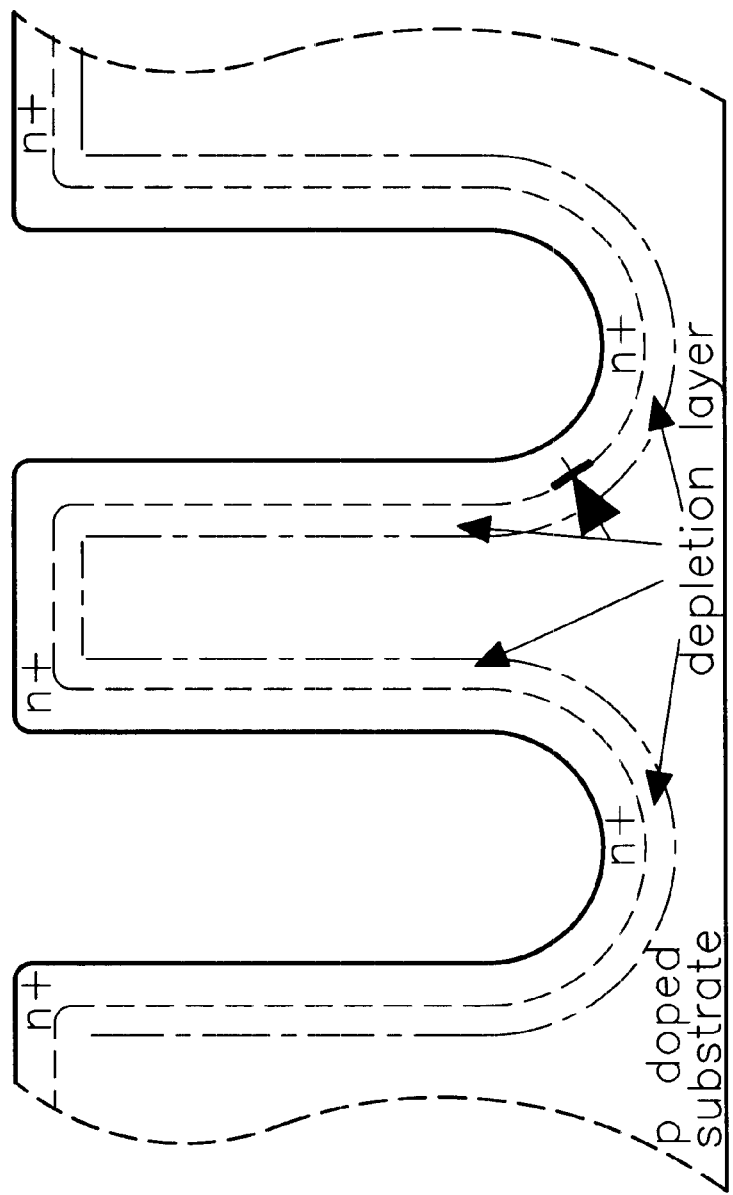
Figure 7F:
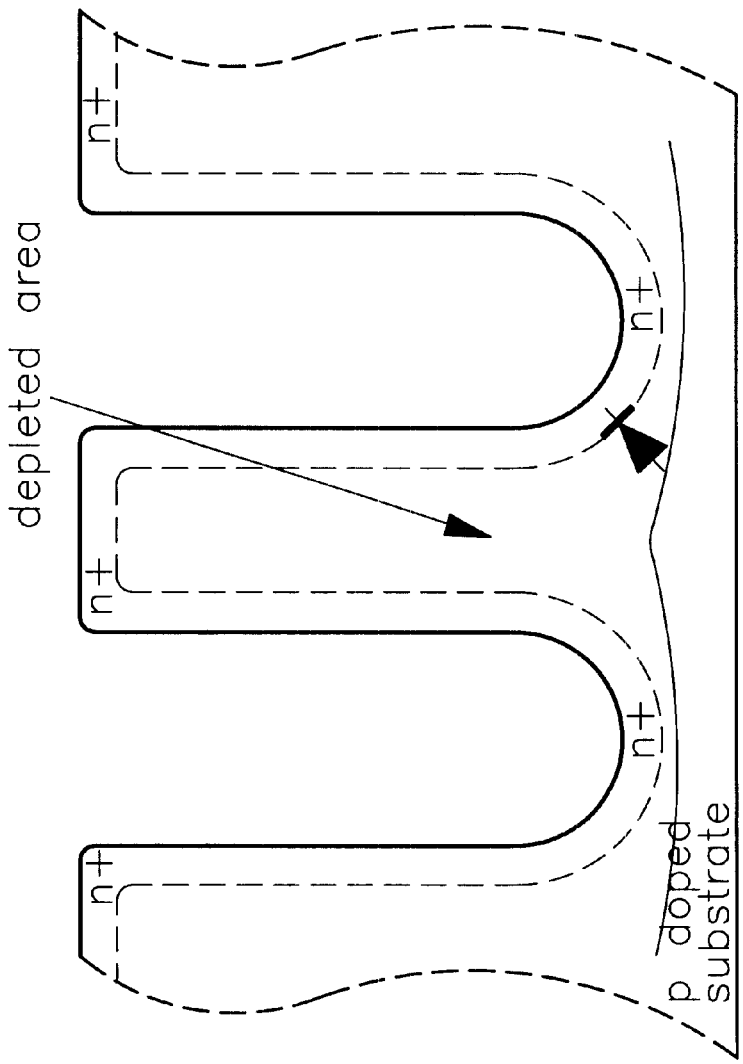

Referring now to FIG. 7e, a region depleted of electrons will build up between the n+ type diffusion layer and the underlying substrate when the bottom electrode an/or diode is reverse biased. The thickness of this depletion layer depends on the magnitude of the bias voltage. As shown in FIG. 7f, when the bias voltage applied to the bottom electrode or diode is increased beyond a certain threshold, the depletion layer increases in thickness to such a point that the depleted layers of adjoining trenches merge, and the adjoining deep trench capacitors act functionally as a single capacitor. Because the aspect ratio of the trenches is relatively large, say between 25 and 500, the surface area of such a fully depleted region is small in respect of the overall resulting capacitance of the n+ type diffusion layer or region. Accordingly, the parasitic capacitance of the n+ type diffusion layer so formed when measured between the bottom plate (or n+ type diffusion region) and the substrate is very small in relation to the overall capacitance measured between the n+ type region and the metal layer shown in FIG. 7d.

In the present invention, the creation of uniform n+ type diffusion layers and regions may be problematic, especially in the deeper portions of the trenches. This is because gas concentration throughout the trenches will ideally be uniform, yet the large aspect ratios of the deep trench capacitors of the present invention, which preferably exceed about 25, may prevent refreshment of the diffusion gases deep in the trench in some cases.

Figure 8A:
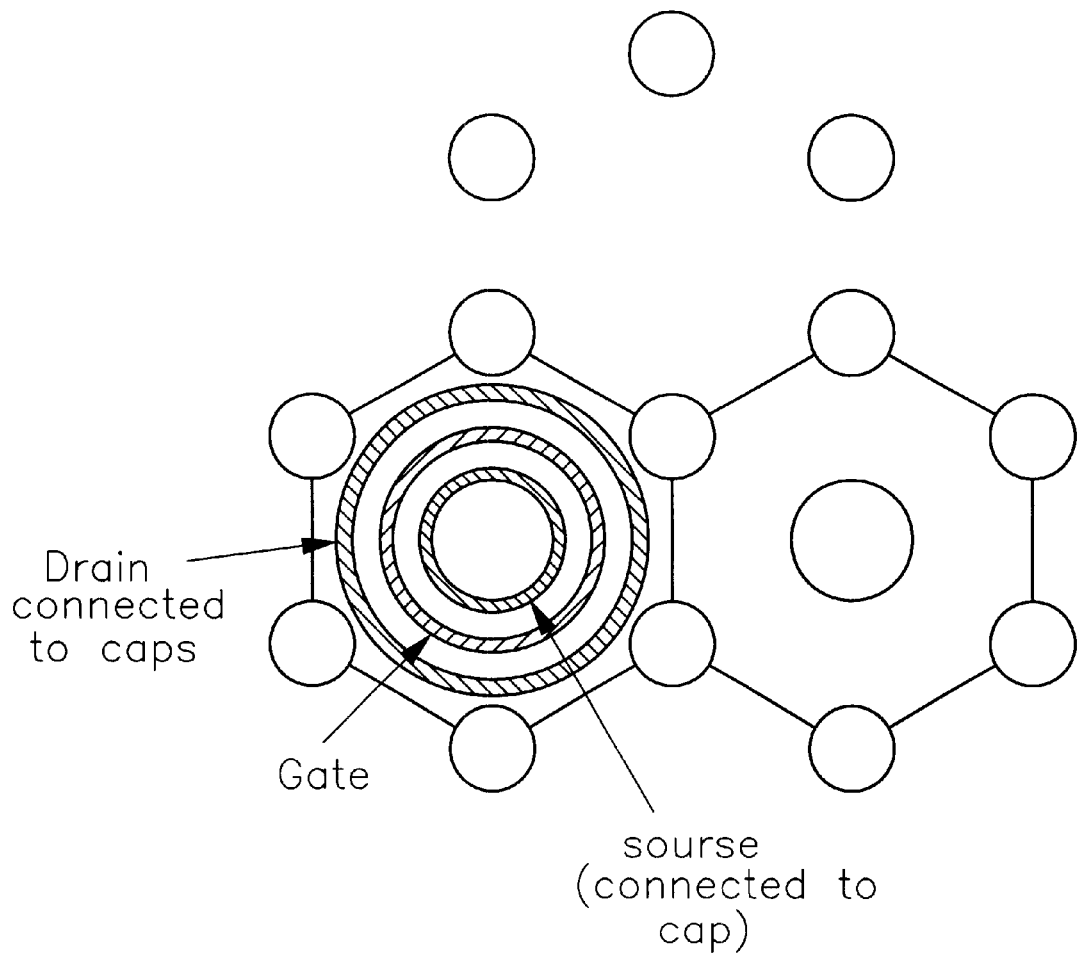
FIGS. 8a and 8b show plan and cross-sectional views of MOS transistors integrated into or near on-chip capacitor arrays of the present invention.
Figure 8B:
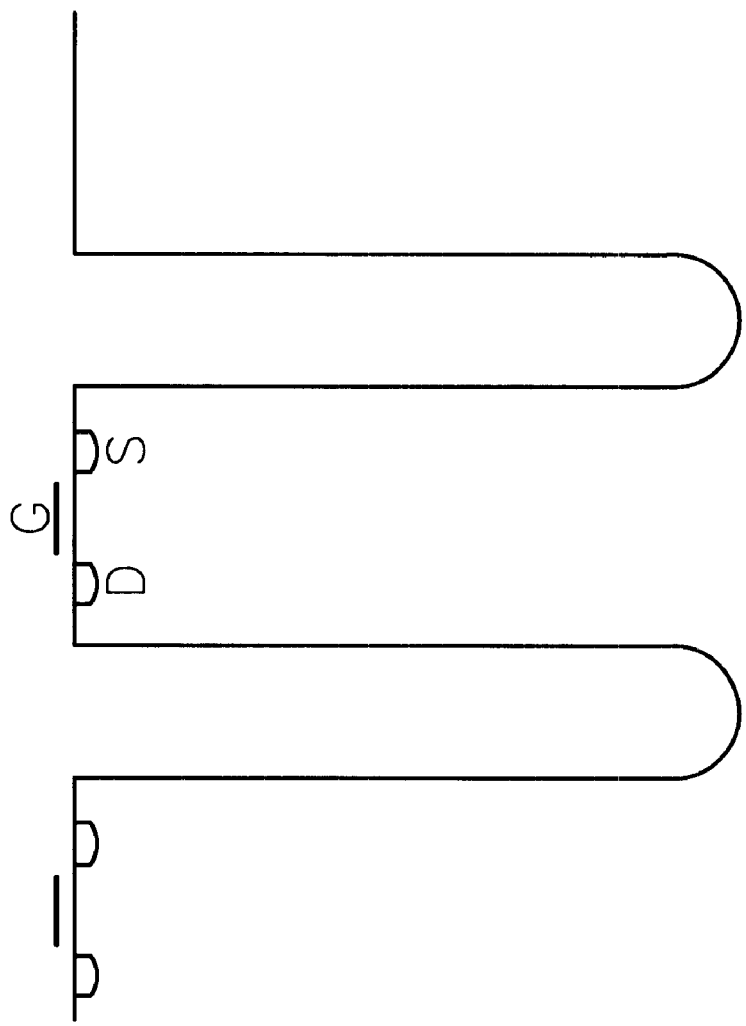

FIGS. 8a and 8b show plan and cross-sectional views of MOS transistors integrated into or near on-chip capacitor arrays of the present invention. It is yet another advantage of the present invention that the high aspect ratio deep trench capacitors of the present invention may be combined with MOS transistors to form integrated high density trench arrays.

In FIG. 7d, the bottom plate of a single capacitor is formed using an n+ type diffusion. A multi-layer structure may be formed, however, where the top plate shown in FIG. 7d is additionally employed as a bottom plate to a second capacitor, and another dielectric layer and another conductive layer are formed atop the top plate to form the second capacitor. A dual capacitor can then be configured to employ the bottom n+ type diffusion layer (which is connected to the top plate of the first capacitor) to double the overall resulting capacitance of the deep trench capacitor by sandwiching the middle metal layer between a second n+ type diffusion layer and a top second metal layer.

The trend towards ever higher chip densities has led to utilizing silicon in three dimensions. Expanding in a vertical direction is the only way to create larger capacitance per unit area. Such a vertical approach to expanding capacitance can lead to a 500-fold increase in capacitance. For example, in a 3 micrometer by 3 micrometer area a 9 micrometer square planar capacitor can be laid out and formed. A trench having a diameter or width of about 3 micrometers and a depth of 500 micrometers has a total area of 9×500 micrometers squared, representing over a 500-fold increase in capacitance.

In the present invention, reduction in hybrid or device size owing to a reduction in the number of wire bonding pads results, in turn, in the lowering of manufacturing errors associated with component placement and contacting. The possibility of large on-chip capacitors reduces the bond pad count and hence chip area and parasitic capacitance. The physical configurations of the deep trench capacitors of the present invention result in very low parasitic capacitances, and accordingly may be employed advantageously to reduce switching losses in capacitive energy conversion schemes.

Additionally, on-chip capacitors of the present invention may be employed to permit electronics to be disposed outside hermetically sealed enclosure 14 of IMD 10. For example, sensing or stimulating electronics may be disposed along portions of atrial or ventricular pacing leads 16 and 18, such as near or at atrial electrodes 20 or 21, or near or at ventricular electrodes 28 or 29, using the on-chip capacitors of the present invention.

The on-chip capacitors of the present invention may thus be employed to create pacing, defibrillation, neurological or other medical electrical leads having, for example, lead-tip intelligence capabilities or active or passive sensors integrated into the lead. Still other applications of the deep trench capacitors of the present invention include medical electrical lead tip pacing and sensing employing, for example, remote high frequency recharge or electrical power techniques, or medical electrical lead tip sensor electronics employing similar recharge or power techniques, as well as distributed medical electrical lead electrode switches.

The areas of the medical device field where the deep trench capacitors of the present invention find the most efficacious application are those areas where deep trench capacitors may be employed to replace discrete off-chip components, such as power supply bypassing and decoupling, sensitive analog circuits where separate ground circuits may be provided by floating deep trench capacitors of the present invention, charge transfer circuits where charge pumps are used to perform energy management functions in stimulation output stage circuitry, charge storage circuits where programmed stimulation voltages are preprogrammed using a storage capacitor connected to a load while stimulation is being applied, and DC blocking output capacitors where a large value capacitor is employed to prevent or impede the flow DC current into the tissue that is to be sensed and/or stimulated.

Although specific embodiments of the invention are described here in some detail, it is to be understood that those specific embodiments are presented for the purpose of illustration, and are not to be taken as somehow limiting the scope of the invention defined in the appended claims to those specific embodiments. It is also to be understood that various alterations, substitutions, and modifications may be made to the particular embodiments of the present invention described herein without departing from the spirit and scope of the appended claims. It is further to be understood that the scope of the present invention is not limited to deep trench capacitors for implantable medical devices, but instead extends to encompass any device, be it a mobile telephone, a laptop computer, a PDA, a computer appliance or any other electronic device which employs the deep trench capacitor technology of the present invention.

In the claims, means plus function clauses are intended to cover the structures and devices described herein as performing the recited function and their equivalents. Means plus function clauses in the claims are not intended to be limited to structural equivalents only, but are also intended to include structures and devices which function equivalently in the environment of the claimed combination.

All printed publications, patents and patent applications referenced hereinabove are hereby incorporated by referenced herein, each in its respective entirety.

We claim:

1. An implantable medical device, comprising:
   (a) an hermetically sealed enclosure;
   (b) electronic circuitry disposed within the hermetically sealed enclosure, and
   (c) means, connected to the electronic circuitry, for measuring at least one physiologic parameter of a patient;
   wherein the electronic circuitry further comprises at least one integrated circuit having at least one deep trench capacitor disposed thereon or therein, the deep trench capacitor further comprising at least one of a reverse-biased bottom electrode and a reverse-biased diode, the deep trench capacitor further having a width and a depth, the ratio of the depth to the width exceeding about ten.

2. The implantable medical device of claim 1, wherein the at least one deep trench capacitor further comprises a p-doped substrate.

3. The implantable medical device of claim 1, wherein the at least one deep trench capacitor further comprises an n-doped substrate.

4. The implantable medical device of claim 1, wherein the ratio of the depth to the width of the at least one deep trench capacitor ranges between about 10 and about 1000.

5. The implantable medical device of claim 1, wherein the ratio of the depth to the width of the at least one deep trench capacitor ranges between about 20 and about 500.

6. The implantable medical device of claim 1, wherein the ratio of the depth to the width of the at least one deep trench capacitor ranges between about 25 and about 500.

7. The implantable medical device of claim 1, wherein the ratio of the depth to the width of the at least one deep trench capacitor exceeds about 25.

8. The implantable medical device of claim 1, wherein the ratio of the depth to the width of the at least one deep trench capacitor ranges exceeds about 50.

9. The implantable medical device of claim 1, wherein the at least one deep trench capacitor is a floating capacitor.

10. The implantable medical device of claim 1, wherein the at least one deep trench capacitor is a non-floating capacitor.

11. The implantable medical device of claim 1, further comprising means for delivering a therapy to the patient.

12. The implantable medical device of claim 1, wherein the implantable medical device is selected from the group consisting of a pacemaker, a defibrillator, a neurological monitor, a neurological stimulator, a drug pump, an insulin monitor, an insulin drug pump, and a stimulator.

13. The implantable medical device of claim 1, wherein the at least one deep trench capacitor is a programmed voltage storage capacitor.

14. The implantable medical device of claim 1, wherein the at least one deep trench capacitor forms a portion of or is electrically connected to a DRAM.

15. The implantable medical device of claim 1, wherein the depth of the deep trench capacitor ranges between about 100 micrometers and about 500 micrometers.

16. The implantable medical device of claim 1, wherein the width of the at least one deep trench capacitor ranges between about 2 micrometers wide and about 5 micrometers wide.

17. The implantable medical device of claim 1, wherein the at least one deep trench capacitor further comprises an n+ type diffusion layer forming a conductive layer.

18. The implantable medical device of claim 1, wherein the at least one deep trench capacitor further comprises a p type diffusion layer forming a conductive layer.

19. The implantable medical device of claim 1, wherein the at least one deep trench capacitor further comprises contact holes etched through portions thereof to permit electrical access and connection to a lower diffusion layer.

20. The implantable medical device of claim 1, wherein the electronic circuitry further comprises MOS transistors.

21. The implantable medical device of claim 20, wherein the MOS transistors are integrated into or near the at least one deep trench capacitor.

22. The implantable medical device of claim 1, further comprising a plurality of deep trench capacitors.

23. The implantable medical device of claim 1, further comprising at least a second integrated circuit having at least a second deep trench capacitor disposed thereon or therein, the second deep trench capacitor further comprising at least one of a second reverse-biased bottom electrode and a second reverse-biased diode, the second deep trench capacitor further having a second width and a second depth, the ratio of the second depth to the second width exceeding about ten, the second integrated circuit being disposed outside the hermetically sealed enclosure.

24. The implantable medical device of claim 1, wherein the at least one deep trench capacitor is included in means for power supply bypassing and decoupling.

25. The implantable medical device of claim 1, wherein the at least one deep trench capacitor is included in an analog circuit having a separate ground circuit.

26. The implantable medical device of claim 1, wherein the at least one deep trench capacitor is included in a charge transfer circuit.

27. The implantable medical device of claim 1, wherein the at least one deep trench capacitor is included in stimulation output stage circuitry.

28. The implantable medical device of claim 1, wherein the at least one deep trench capacitor is included in charge storage circuitry.

29. The implantable medical device of claim 1, wherein the at least one deep trench capacitor is included in programmed stimulation voltage circuitry.

30. The implantable medical device of claim 1, wherein the at least one deep trench capacitor is included in a storage capacitor circuit.

31. The implantable medical device of claim 1, wherein the at least one deep trench capacitor is included in DC blocking output circuitry.

32. The implantable medical device of claim 1, wherein the at least one deep trench capacitor has a capacitance ranging between about 10 nF and about 100 uF.

33. The implantable medical device of claim 1, wherein the at least one deep trench capacitor has a capacitance exceeding about 10 nF.

34. The implantable medical device of claim 1, wherein the at least one deep trench capacitor has a capacitance less than about 100 uF.

35. The implantable medical device of claim 1, wherein the at least one deep trench capacitor forms a multi-layer deep trench capacitor.

36. A method of making an implantable medical device, the implantable medical device comprising an hermetically sealed enclosure, electronic circuitry disposed within the hermetically sealed enclosure, and means, connected to the electronic circuitry, for measuring at least one physiologic parameter of a patient, wherein the electronic circuitry further comprises at least one integrated circuit having at least one deep trench capacitor disposed thereon or therein, the deep trench capacitor further comprising at least one of a reverse-biased bottom electrode and a reverse-biased diode, the deep trench capacitor further having a width and a depth, the ratio of the depth to the width exceeding about ten, the method comprising:

(a) forming the at least one deep trench capacitor;

(b) disposing the electronic circuitry within the enclosure; and (c) hermetically sealing the enclosure.

* * * * *